United States Patent
Tsai

(10) Patent No.: US 11,657,941 B2
(45) Date of Patent: May 23, 2023

(54) RESONANT ENERGY STABILIZER

(71) Applicant: Ching-Cheng Tsai, Taichung (TW)

(72) Inventor: Ching-Cheng Tsai, Taichung (TW)

( * ) Notice: Subject to any disclaimer, the term of this patent is extended or adjusted under 35 U.S.C. 154(b) by 47 days.

(21) Appl. No.: 17/535,739

(22) Filed: Nov. 26, 2021

(65) Prior Publication Data

US 2023/0055001 A1 Feb. 23, 2023

(30) Foreign Application Priority Data

Aug. 20, 2021 (TW) .................................. 110209846

(51) Int. Cl.
*H01F 7/06* (2006.01)
*H01F 1/057* (2006.01)

(52) U.S. Cl.
CPC ............. *H01F 7/064* (2013.01); *H01F 1/057* (2013.01)

(58) Field of Classification Search
CPC .................................. H01F 7/064; H01F 1/057
USPC ....................................................... 361/231
See application file for complete search history.

(56) References Cited

FOREIGN PATENT DOCUMENTS

| CN | 101239221 A | * | 8/2008 |
| TW | 615562 U | * | 8/2021 |

OTHER PUBLICATIONS

Machine translation of Cai Taiwanese Patent Document TW M615562 U Aug. 11, 2021 (Year: 2021).*
Machine Translation of Lin Chinese Patent Document CN 101239221 A Aug. 13, 2008 (Year: 2008).*

* cited by examiner

*Primary Examiner* — Kevin J Comber

(57) ABSTRACT

A resonant energy stabilizer contains: a body, a lid, a mineral crystal, the current amplifier, and a medium frequency current device. The body includes an accommodation chamber. The lid includes an accommodating room. The mineral crystal includes a recess configured to accommodate a sapphire for producing far-infrared waves of electrostatic pulse. The recess is surrounded by a white crystal, a citrine and a green crystal which are surrounded by multiple titanium crystals, and a first magnetite is located above the white crystal, the citrine and the green crystal. The current amplifier includes multiple plasma pieces stacked together to increase a distance of the far-infrared waves of the electrostatic pulse, and each plasma piece has a copper coil layer, a red brass patch, and a red copper sheet. The medium frequency current device includes multiple second magnetites, an input segment, a central processing unit, a booster, and an output segment.

6 Claims, 8 Drawing Sheets

RESONANT ENERGY STABILIZER

FIELD OF THE INVENTION

The present invention relates to a resonant energy stabilizer related to a micro-energy adjustment tool that is capable of attracting earth energy and achieving harmony and resonance in human society, and more particularly to be applicable for resonant stabilization by way of electrostatic pulse waves.

BACKGROUND OF THE INVENTION

After the industrial revolution, people have greatly developed land, drilled through tunnels, leveled hills, filled streams, built dams, broken veins, high-rise buildings like concrete forests, high-voltage electrical towers and electromagnetic radiation from WiFi, etc. The man-made facilities interfered with the earth's original yin and yang balance of positive and negative charges and the balance movement of the true breath, which is the vitality of the earth's energy brings to all living beings.

As the earth's ecological environment has been overexploited by humans, the earth's life energy field has also been fragmented. This is the side effect of current social progress and industrial development. Although wealth is increasing day by day, the health and happiness of the body are paid a painful price, and the entire country and society will be affected.

The present invention has arisen to mitigate and/or obviate the afore-described disadvantages.

SUMMARY OF THE INVENTION

One aspect of the present invention is to provide a resonant energy stabilizer which facilitates harmony and resonance of all beings and the earth.

To obtain the above aspect, a resonant energy stabilizer provided by the present invention contains: a body, a lid, a mineral crystal, the current amplifier, and a medium frequency current device.

The body includes an accommodation chamber defined in the body and configured to receive the mineral crystal and the current amplifier.

The lid covers an opening of a top of the body, and the lid includes an accommodating room defined in the lid and configured to receive the medium frequency current device.

The mineral crystal is received in the accommodation chamber of the body, the mineral crystal includes a recess defined on a center thereof and configured to accommodate a sapphire for producing far-infrared waves of electrostatic pulse, wherein the recess is surrounded by a white crystal, a citrine, and a green crystal, wherein the white crystal, the citrine and the green crystal are surrounded by multiple titanium crystals to accelerate a spreading of the far-infrared waves of the electrostatic pulse, and a first magnetite is located above the white crystal, the citrine and the green crystal so as to enhance a magnetic field.

The current amplifier includes multiple plasma pieces stacked together to increase a distance of the far-infrared waves of the electrostatic pulse, and each plasma piece has a copper coil layer, a red brass patch stacked with the copper coil layer, and a red copper sheet defined between the copper coil layer and the red brass patch, wherein the current amplifier further includes an electric wire which has a plasma connection wire electrically connected with an upmost red brass patch, a middle red brass patch, and a lowermost red brass patch in series to produce radioactive magnetic field waves.

The medium frequency current device includes multiple second magnetites which are attached on the upmost red brass patch, the medium frequency current device further includes an input segment, a central processing unit, a booster, and an output segment, wherein the input segment is connected with a power supply, and the central processing unit and the booster increase electric voltages to produce a high voltage and low electric currents via the multiple second magnetites and the multiple red brass patches to generate the radioactive magnetic field wave, then the radioactive magnetic field wave is increased to enhance the magnetic field increased by the first magnetite, the magnetic field strikes the sapphire for producing the far-infrared waves of the electrostatic pulse, wherein the white crystal, the citrine, the green crystal and the multiple titanium crystals accelerate the spreading of the far-infrared waves of the electrostatic pulse, such that the mineral crystal refracts and amplifies the far-infrared waves of the electrostatic pulse, and the distance of the far-infrared waves of the electrostatic pulse is increased by the multiple plasma pieces of the current amplifier.

Preferably, the mineral crystal is quartz.

Preferably, the multiple second magnetites are made of NdFeB.

Preferably, a diameter of the first magnetite is more than a diameter of the recess of the mineral crystal.

Preferably, the current amplifier includes three plasma pieces stacked together, and each plasma piece is made of three stacking layers, such that the three plasma pieces have nine stacking layers, wherein each plasma piece has neutrons for releasing the radioactive magnetic field waves.

Preferably, each copper coil layer has multiple copper wires winded together and an insulation layer covering the multiple copper wires.

DETAILED DESCRIPTION OF THE PREFERRED EMBODIMENTS

Figure 1:
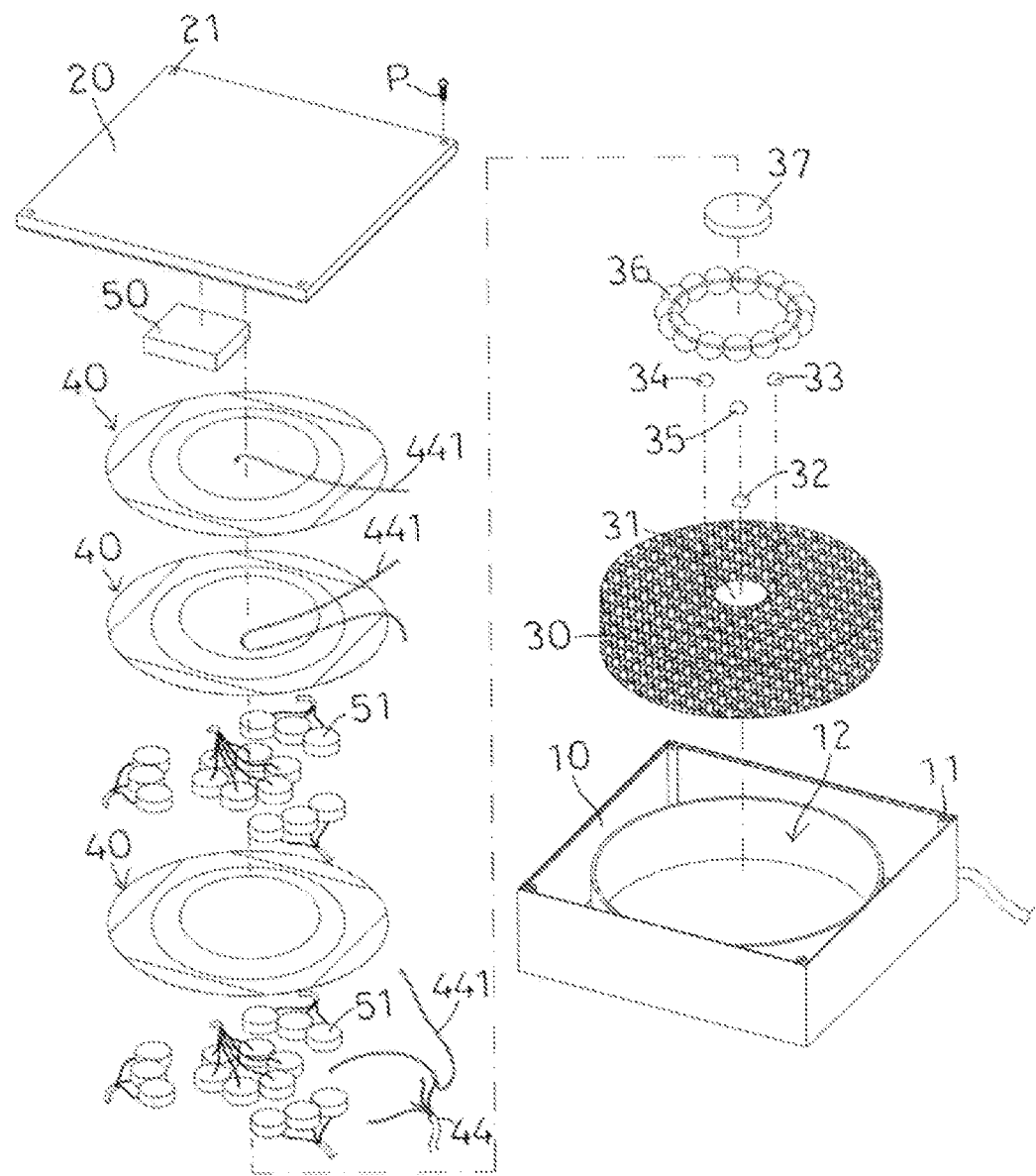
FIG. 1 is a perspective view showing the exploded components of a resonant energy stabilizer according to a preferred embodiment of the present invention.
Figure 2:
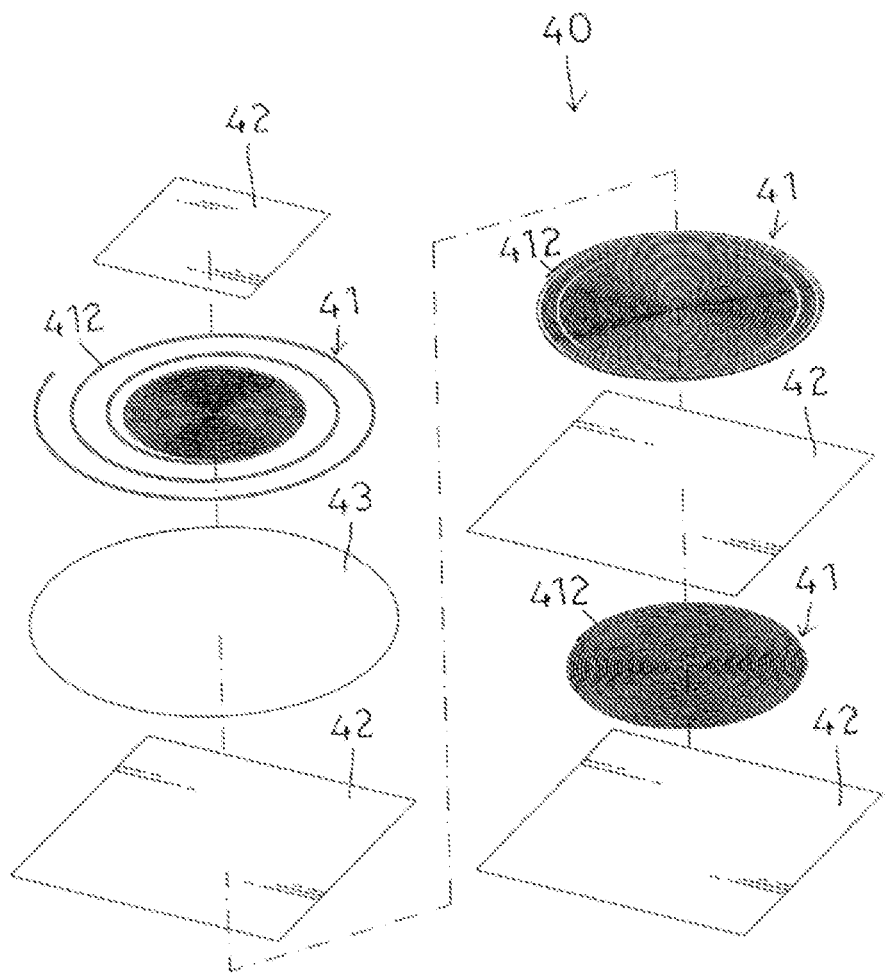
FIG. 2 is a perspective view showing the exploded components of a current amplifier of the resonant energy stabilizer according to the preferred embodiment of the present invention.
Figure 3:
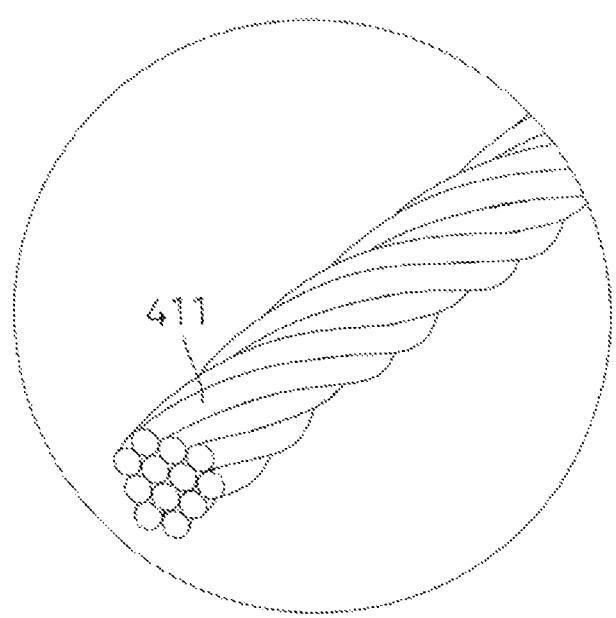
FIG. 3 is a perspective view showing the assembly of a copper wire coil of the resonant energy stabilizer according to the preferred embodiment of the present invention.
Figure 4:
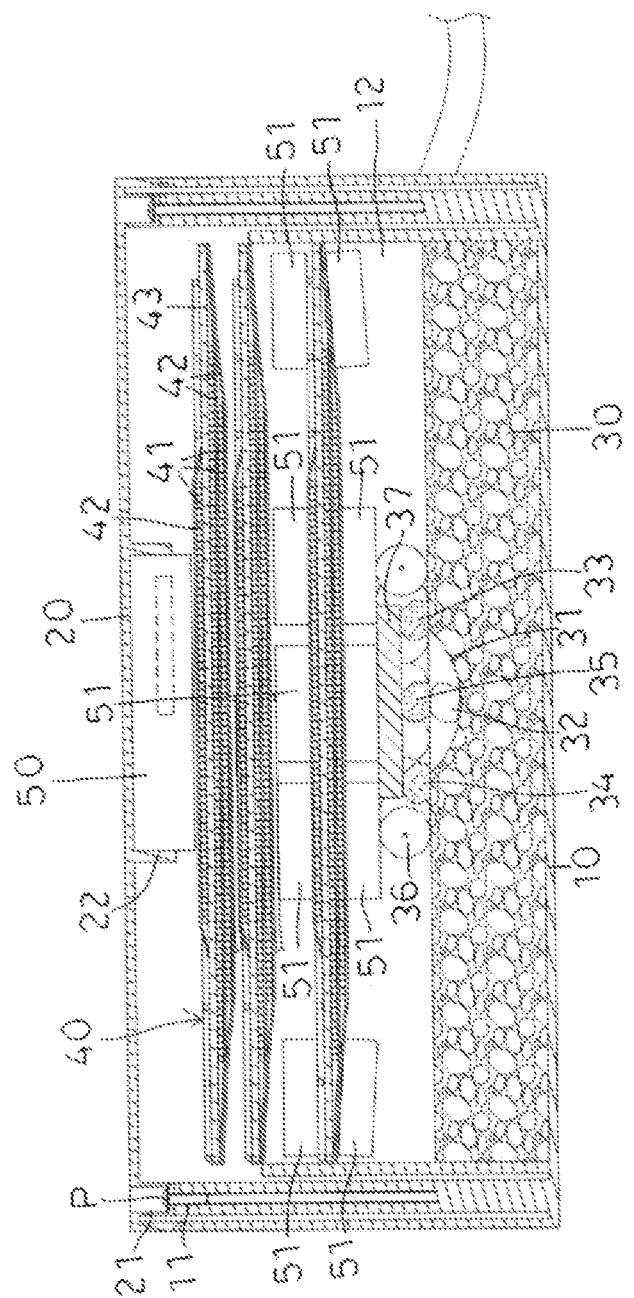
FIG. 4 is a cross sectional view showing the assembly of the resonant energy stabilizer according to the preferred embodiment of the present invention.

FIG. 1 is a perspective view showing the exploded components of a resonant energy stabilizer according to a preferred embodiment of the present invention. FIG. 2 is a perspective view showing the exploded components of a current amplifier of the resonant energy stabilizer according to the preferred embodiment of the present invention. FIG. 3 is a perspective view showing the assembly of a copper wire coil of the resonant energy stabilizer according to the preferred embodiment of the present invention. FIG. 4 is a cross sectional view showing the assembly of the resonant energy stabilizer according to the preferred embodiment of the present invention.

The resonant energy stabilizer of the present invention comprises: a body 10, a lid 20, a mineral crystal 30, the current amplifier 40, and a medium frequency current device 50.

The body 10 includes a bottom, a peripheral wall extending upward from the bottom thereof, and an opening defined on a top of the body 10, wherein the body 10 further includes multiple receiving orifices 11 formed on four corners of the peripheral wall of the body 10 and screwing with multiple screws P which are screwed with the lid 20, and a circular accommodation chamber 12 defined in the body 10 and configured to receive the mineral crystal 30 and the current amplifier 40.

The lid 20 covers the opening of the top of the body 10, and the lid 20 includes multiple through orifices 21 defined on four corners thereof and corresponding to the multiple receiving orifices 11 of the body 10, such that the multiple screws P are screwed with the multiple receiving orifices 11 of the body 10 via the multiple through orifice 21, wherein the lid 20 further includes an accommodating room 22 defined in the lid 20 and configured to receive the medium frequency current device 50.

The mineral crystal 30 is quartz and is received in the circular accommodation chamber 12 of the body 10, the mineral crystal 30 includes a recess 31 defined on a center thereof and configured to accommodate a sapphire 32 for producing far-infrared waves of electrostatic pulse, wherein the mineral crystal 30 has a piezoelectric effect so that when the quartz is forced by an alternating electric field, the quartz produces a mechanical vibration, and when a frequency of the alternating electric field is identical to a frequency of the quartz, the mechanical vibration strengthens, thus producing a resonance reaction of the mineral crystal. Thereby, a crystal oscillator is capable of replacing an inductance capacitance (LC) circuit, a resonant circuit, and a wave filter to obtain a small size, a compact weight, a high reliability, and a high frequency stability and to increase an far-infrared waves amplification and a refraction power of the electrostatic pulse.

The recess 31 is surrounded by a white crystal 33, a citrine 34, and a green crystal 35, wherein the white crystal 33, the citrine 34 and the green crystal 35 are surrounded by multiple titanium crystals 36 for activating tissue cells and meridian, and the white crystal 33, the citrine 34, the green crystal 35 and the multiple titanium crystals 36 accelerate a spreading of the far-infrared waves of the electrostatic pulse. Furthermore, a first magnetite 37 is located above the white crystal 33, the citrine 34 and the green crystal 35, wherein a diameter of the first magnetite 37 is more than a diameter of the recess 31 of the mineral crystal 30 so as to enhance a magnetic field.

Figure 5:
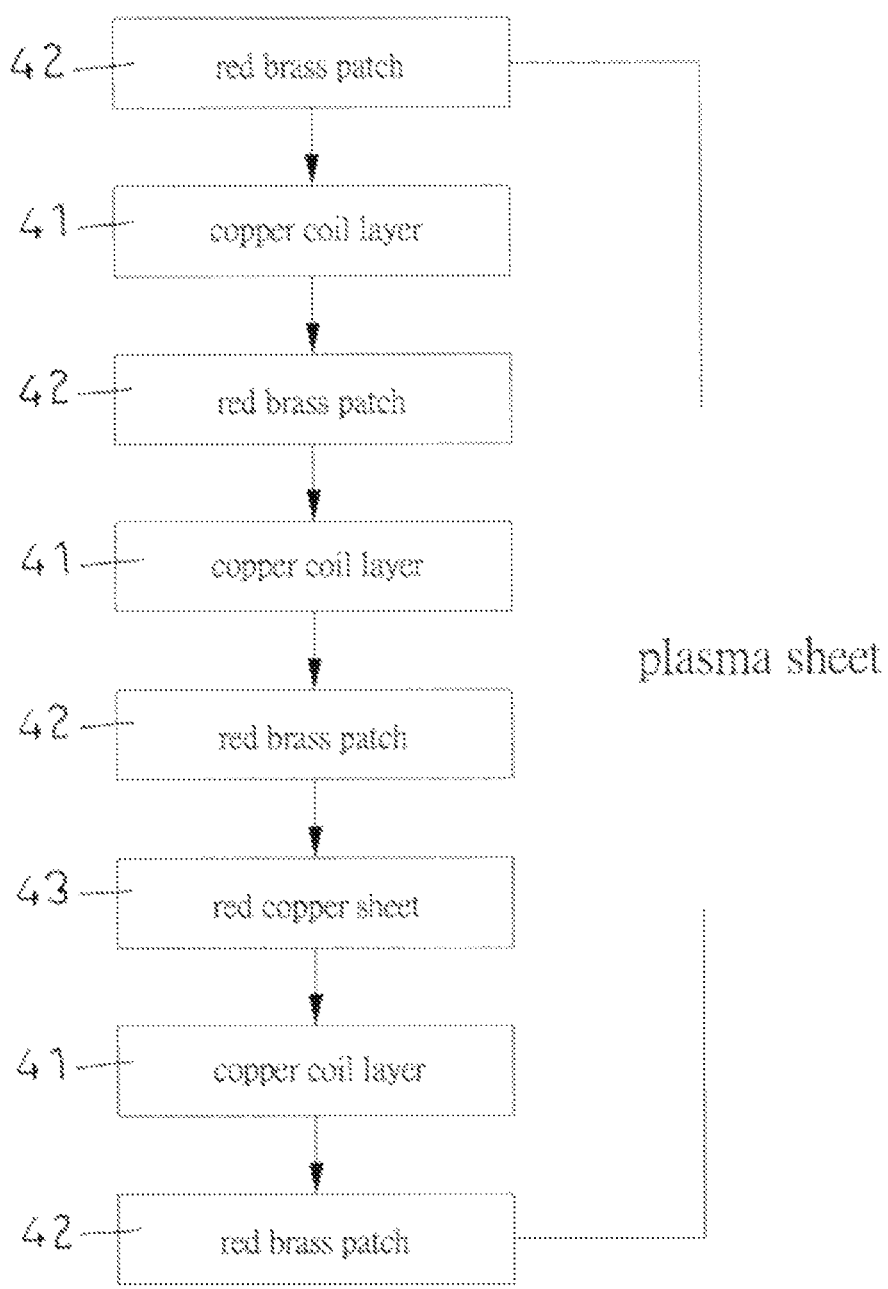
FIG. 5 is a block diagram of each of the three plasma pieces of the resonant energy stabilizer according to the preferred embodiment of the present invention.

The current amplifier 40 includes three plasma pieces stacked together. FIG. 5 is a block diagram of each of the three plasma pieces of the resonant energy stabilizer according to the preferred embodiment of the present invention. Each plasma piece is made of three stacking layers, so the three plasma pieces have nine stacking layers, wherein each plasma piece has neutrons for releasing magnetic field waves to increase a distance and a range of the far-infrared waves of the electrostatic pulse. Each plasma piece has three copper coil layers 41, four red brass patches 42, and a red copper sheet 43. Each copper coil layer 41 has multiple copper wires 411 winded together and an insulation layer 412 covering the multiple copper wires 411. Each red brass patch 42 is formed in a plate shape and is stacked with each copper coil layer 41, and the red copper sheet 43 is defined between a first copper coil layer 41 and a first red brass patch 42, an upmost red brass patch 42 and a lowermost red brass patch 42 are attached with one of multiple second magnetites 51 (made of NdFeB) to produce radioactive magnetic field waves. The current amplifier 40 further includes an electric wire 44 which has a plasma connection wire 441 electrically connected with the upmost red brass patch 42, a middle red brass patch 42, and the lowermost red brass patch 42 in series.

Figure 6:
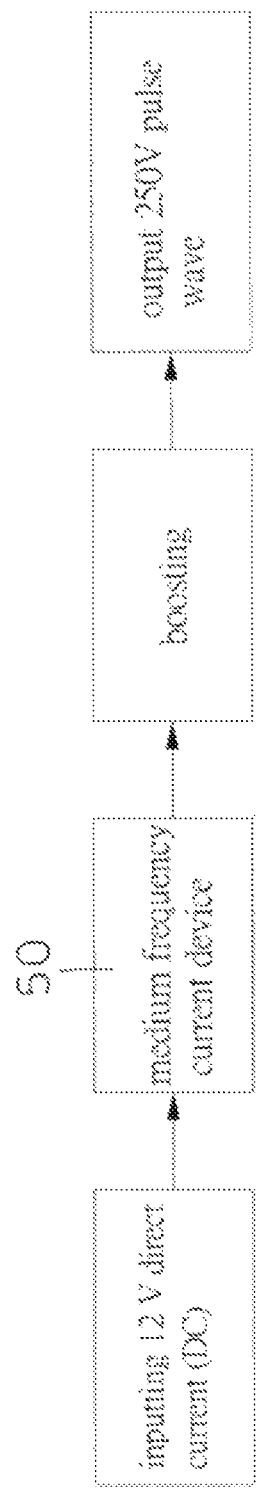
FIG. 6 is a block diagram of the medium frequency current device of the resonant energy stabilizer according to the preferred embodiment of the present invention.

FIG. 6 is a block diagram of the medium frequency current device of the resonant energy stabilizer according to the preferred embodiment of the present invention. The medium frequency current device 50 includes the multiple second magnetites 51 which are attached on the upmost red brass patch 42. The medium frequency current device 50 produces low-voltage interference currents to stimulate nerves, thus releasing muscles alternately. The medium frequency current device 50 further includes an input segment DC 12V, a central processing unit (CPU), a booster, and an output segment 250V, wherein the input segment DC 12V is connected with a power supply, and the CPU and the booster increase electric voltages to produce an output voltage of 250V pulse wave, thus forming low electric currents.

Figure 7:
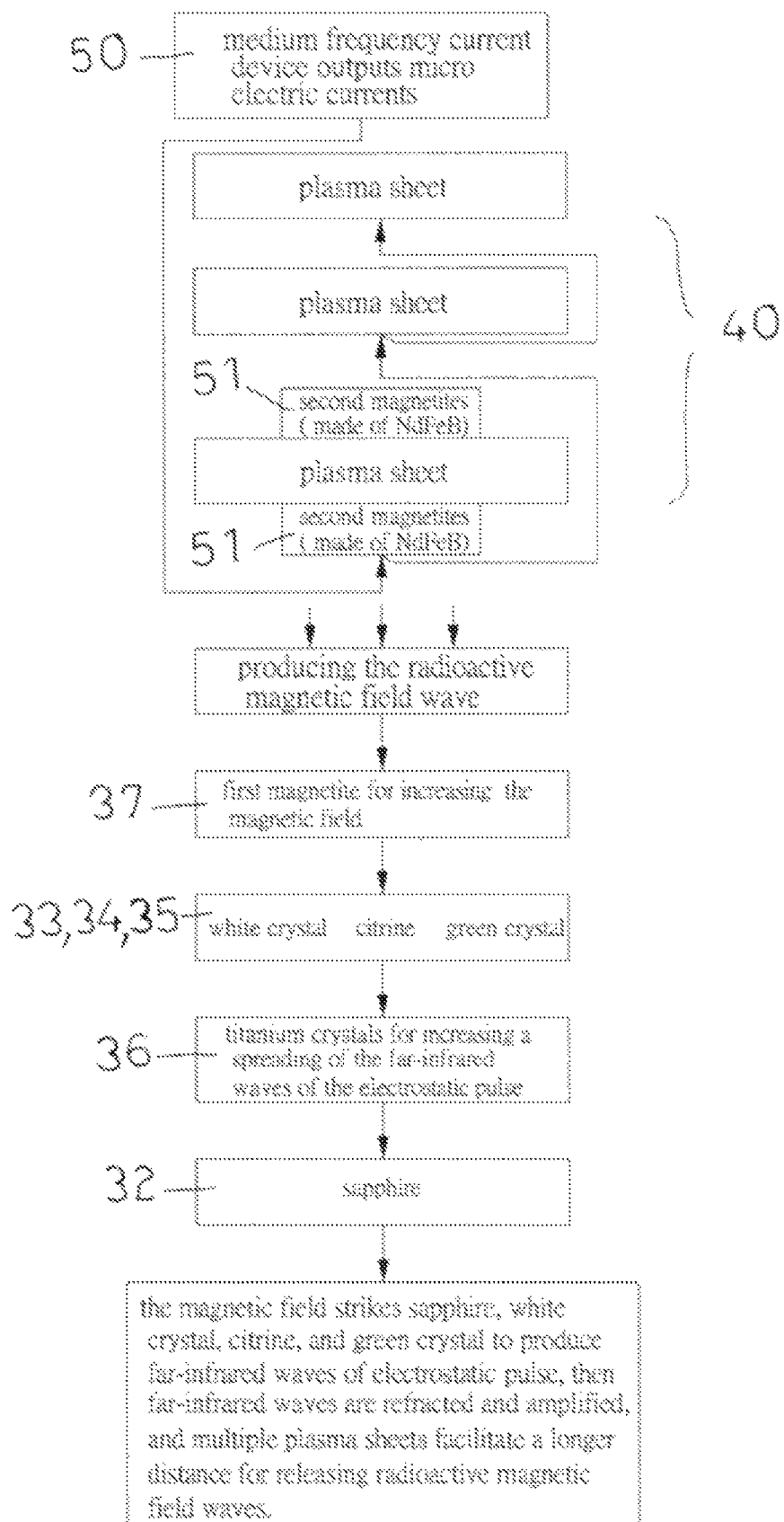
FIG. 7 is a flow chart of the operation of the resonant energy stabilizer according to the preferred embodiment of the present invention.

FIG. 7 is a flow chart of the operation of the resonant energy stabilizer according to the preferred embodiment of the present invention.

Figure 8:
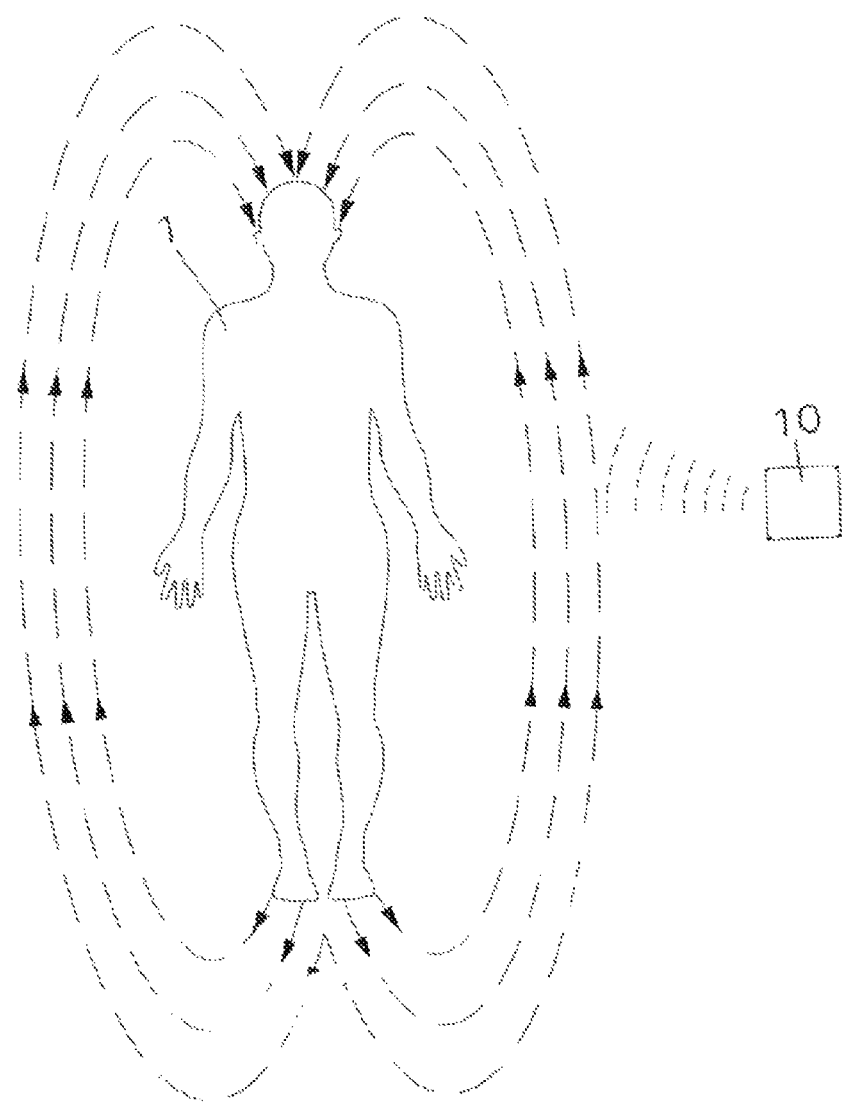
FIG. 8 is a schematic view showing the application of the resonant energy stabilizer according to the preferred embodiment of the present invention.

FIG. 8 is a schematic view showing the application of the resonant energy stabilizer according to the preferred embodiment of the present invention. When the medium frequency current device 50 outputs micro electric currents via the multiple second magnetites 51 and the four red brass patches 42 to produce the radioactive magnetic field wave, the radioactive magnetic field wave is increased to enhance the magnetic field increased by the first magnetite 37, and the magnetic field strikes the sapphire 32 for producing far-infrared waves of electrostatic pulse, and the white crystal 33, the citrine 34, the green crystal 35 and the multiple titanium crystals 36 accelerate the spreading of the far-infrared waves of the electrostatic pulse. Thereby, the mineral crystal 30 refracts and amplifies the far-infrared waves of the electrostatic pulse, and the distance of the far-infrared waves of the electrostatic pulse is increased by the three plasma pieces of the current amplifier 40, such that the far-infrared waves of the electrostatic pulse produces a stable resonance to a user 1, thus enhancing a stable energy to the user 1 as well.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A resonant energy stabilizer comprising: a body, a lid, a mineral crystal, a current amplifier, and a medium frequency current device;
   wherein the body includes an accommodation chamber defined in the body and configured to receive the mineral crystal and the current amplifier;
   wherein the lid covers an opening of a top of the body, and the lid includes an accommodating room defined in the lid and configured to receive the medium frequency current device;
   wherein the mineral crystal is received in the accommodation chamber of the body, the mineral crystal includes a recess defined on a center thereof and configured to accommodate a sapphire for producing far-infrared waves of electrostatic pulse, wherein the recess is surrounded by a white crystal, a citrine, and a green crystal, wherein the white crystal, the citrine and the green crystal are surrounded by multiple titanium crystals to accelerate a spreading of the far-infrared waves of the electrostatic pulse, and a first magnetite is located above the white crystal, the citrine and the green crystal so as to enhance a magnetic field;
   wherein the current amplifier includes multiple plasma pieces stacked together to increase a distance of the far-infrared waves of the electrostatic pulse, and each plasma piece has a copper coil layer, a red brass patch stacked with the copper coil layer, and a red copper sheet defined between the copper coil layer and the red brass patch, wherein the current amplifier further includes an electric wire which has a plasma connection wire electrically connected with an upmost red brass patch, a middle red brass patch, and a lowermost red brass patch in series to produce radioactive magnetic field waves;
   wherein the medium frequency current device includes multiple second magnetites which are attached on the upmost red brass patch, the medium frequency current device further includes an input segment, a central processing unit, a booster, and an output segment, wherein the input segment is connected with a power supply, and the central processing unit and the booster increase electric voltages to produce a high voltage and low electric currents via the multiple second magnetites and the multiple red brass patches to generate the radioactive magnetic field wave, then the radioactive magnetic field wave is increased to enhance the magnetic field increased by the first magnetite, the magnetic field strikes the sapphire for producing the far-infrared waves of the electrostatic pulse, wherein the white crystal, the citrine, the green crystal and the multiple titanium crystals accelerate the spreading of the far-infrared waves of the electrostatic pulse, such that the mineral crystal refracts and amplifies the far-infrared waves of the electrostatic pulse, and the distance of the far-infrared waves of the electrostatic pulse is increased by the multiple plasma pieces of the current amplifier.

2. The resonant energy stabilizer as claimed in claim 1, wherein the mineral crystal is quartz.

3. The resonant energy stabilizer as claimed in claim 1, wherein the multiple second magnetites are made of NdFeB.

4. The resonant energy stabilizer as claimed in claim 1, wherein a diameter of the first magnetite is more than a diameter of the recess of the mineral crystal.

5. The resonant energy stabilizer as claimed in claim 1, wherein the current amplifier includes three plasma pieces stacked together, and each plasma piece is made of three stacking layers, such that the three plasma pieces have nine stacking layers, wherein each plasma piece has neutrons for releasing the radioactive magnetic field waves.

6. The resonant energy stabilizer as claimed in claim 1, wherein each copper coil layer has multiple copper wires winded together and an insulation layer covering the multiple copper wires.

* * * * *